(12) United States Patent
Van Dalen et al.

(10) Patent No.: US 8,142,459 B2
(45) Date of Patent: Mar. 27, 2012

(54) ANTERIOR CAPSULOTOMY DEVICE AND PROCEDURE

(75) Inventors: Johan T. W. Van Dalen, Tucson, AZ (US); Dan D. Carda, Tucson, AZ (US)

(73) Assignee: Eye Care and Cure Pte. Ltd, Singapore (SG)

( * ) Notice: Subject to any disclaimer, the term of this patent is extended or adjusted under 35 U.S.C. 154(b) by 295 days.

(21) Appl. No.: 12/510,528

(22) Filed: Jul. 28, 2009

(65) Prior Publication Data

US 2011/0029005 A1     Feb. 3, 2011

(51) Int. Cl.
*A61F 9/00*     (2006.01)
(52) U.S. Cl. .......................................... 606/166; 604/22
(58) Field of Classification Search .................. 606/166, 606/167, 170, 171, 177, 5; 604/22
See application file for complete search history.

(56) References Cited

U.S. PATENT DOCUMENTS

| | | | |
|---|---|---|---|
| 2,249,906 A * | 7/1941 | Longoria ...................... | 606/166 |
| 3,756,128 A * | 9/1973 | Armstrong et al. ........... | 493/290 |
| 5,423,841 A | 6/1995 | Kornfeld | |
| 5,591,185 A * | 1/1997 | Kilmer et al. ................. | 606/166 |
| 2004/0092982 A1 | 5/2004 | Sheffer | |
| 2004/0116950 A1 | 6/2004 | Eibschitz-Tsimhoni | |

FOREIGN PATENT DOCUMENTS

DE     10220253     11/2002

OTHER PUBLICATIONS

International Search Report and Written Opinion dated Sep. 16, 2010.

* cited by examiner

*Primary Examiner* — Victor Nguyen
(74) *Attorney, Agent, or Firm* — Dale F. Regelman; Quarles & Brady LLP

(57) ABSTRACT

A device for performing an anterior capsulotomy procedure and a method using the same is presented. The device includes a body having a rotatable cutting element rotatably disposed on the proximal end. The cutting element further includes multiple surgical blades. In certain embodiments, the device further includes an arcuate member, wherein two surgical blades are attached at opposing ends and extend outwardly from the arcuate member. In using the device to perform an anterior capsulotomy, the device is inserted into an incision made in an eye and the surgical blades are brought in contact with the anterior capsule wall. The anterior capsule wall is then transformed by rotating the rotatable cutting element, creating an aperture there through.

9 Claims, 6 Drawing Sheets

ANTERIOR CAPSULOTOMY DEVICE AND PROCEDURE

BACKGROUND

The present invention relates generally to medical devices and more particularly to medical devices for performing an anterior capsulotomy (capsulorrhexis).

During cataract surgery, or removal and replacement of the natural lens of the eye, a surgeon must enter the globe, using a small millimeter blade, to access the cataract, which commonly involves the centermost layer (the cortex) of the lens. Most often, a clear corneal suture-less incision of 3 mm or less is made. The anterior chamber is then filled with a viscoelastic substance to protect the cornea during cataract surgery and to maintain the integrity of the anterior chamber when necessary. An additional incision called a paracentesis is placed at approximately 90° (ninety degrees) to facilitate the manipulation of the cataract during phaco emulsification, a process that utilizes ultrasound to gently suction out the cataract.

Prior to the suctioning of the cataract, an opening in the capsule is needed to allow for the use of devices required to effectively remove cortex and mucleus from the capsule. It is of the utmost importance that the integrity of the anterior (after anterior capsulotomy) and posterior capsule is maintained. Post-operatively the capsular envelope serves as a retainer for an artificial implant (intra-ocular lens (IOL). Without the capsule, or if the structure is compromised, the use of a posterior implant may be contraindicted since the capsule provides the support needed to keep the artificial lens in place.

There are two prior art methods of performing an anterior capsulotomy. The first, referred to as the "can opener" technique, is an older procedure before more modern techniques and advanced equipment (such as the Utrata forceps) became available. This procedure involves the surgeon making a series of small, connected punctures using a cystotome, or bent needle, running 360° (three-hundred and sixty degrees) around the anterior portion of the capsule, resulting in an opening that resembles the appearance of the top of an open can.

The second method requires the surgeon to nick the anterior portion of the capsule with a cystotome to create a tear in the membrane. Using an Utrata forceps, an edge of the tear is grasped and guided to create a circular aperture in the surface of the anterior capsule.

Both techniques require significant skill on the part of the surgeon and generally take years to master. Even a slight error, can result in a devastating prognosis for the patient. If the capsulotomy is too small, the cataract may not be removed sufficiently, If the capsulotomy is too large or the anterior capsule tears during the process, extending and resulting in a posterior capsular tear, the capsule may not be able to support the artificial lens implant or, worse yet, there may be a loss of the vitreous. If a vitreous loss occurs an immediate vitrectomy is required, which has the potential of a lifetime of visual impairment or blindness for the patient. Furthermore, the use of many newer intraocular lenses require that the anterior capsulotomy be performed such that a circular opening with a predetermined diameter be made.

Thus, the prior art methods for performing anterior capsulotomies possess inherent deficiencies that increase the likelihood of complications and decrease the procedure's safety. Therefore, there is a need for a means of reliably and safely performing an anterior capsulotomy.

SUMMARY

In one implementation, a device for performing an anterior capsulotomy procedure is presented, wherein the device is disposable after a single use. The device includes a body having a rotatable cutting element rotatably disposed on the proximal end.

In another implementation, the rotatable cutting element of the device further includes an arcuate member having opposing first and second ends. A first surgical blade is attached to the first end and the second surgical blade is attached to the second end, the surgical blades extending outwardly from the arcuate member.

Another implementation, a method of performing an anterior capsulotomy is presented. The method includes making an incision in an eye. A device is then provided and inserted into the incision. The device has a rotatable cutting element disposed on the proximal end of the device, the cutting element having multiple blades and being operatively coupled to an actuator. The actuator can be moved from a first to a second position, causing the rotatable cutting element to rotate. The method further includes bringing the surgical blades in contact with the anterior capsule wall and transforming it by moving the actuator from the first to the second position, thereby creating an aperture therein.

And yet another embodiment, the rotatable element of the provided device further includes an arcuate member having opposing first and second ends. A first surgical blade is attached to the first end and the second surgical blade is attached to the second end, the surgical blades extending outwardly from the arcuate member. The method of performing the anterior capsulotomy further includes rotating the arcuate member about 180 degrees.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The anterior capsulotomy device of the present invention is illustrated in FIGS. 5-9. For illustrative purposes only, FIGS. 1-4 are provided depicting the prior art methodology.

Figure 1:
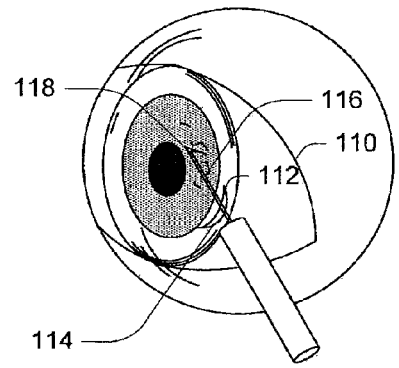
FIG. 1 is a prospective view of a human eyeball illustrating the prior art practice of performing an anterior capsulotomy.

Referring now to FIG. 1, a human eye 110 is depicted having an anterior capsule 122 (FIG. 3) exposed through the pupil 128 of the overlying iris 132, and the sclera 130 (FIG. 4) circumferentially surrounding iris 132. The cornea 114 overlies anterior capsule 122, pupil 128, and iris. Historically, an anterior capsulotomy is performed by making an initial limbal incision 112 in the limbus zone where sclera and iris meet. Alternatively, a clear corneal incision may be made instead.

Figure 2:
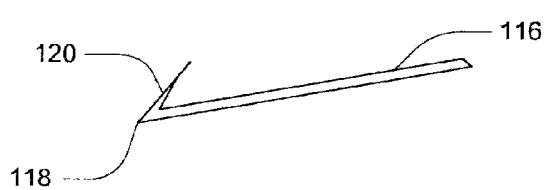
FIG. 2 is an exemplary stylet or needle used to perform an anterior capsulotomy according to the prior art method.
Figure 3:
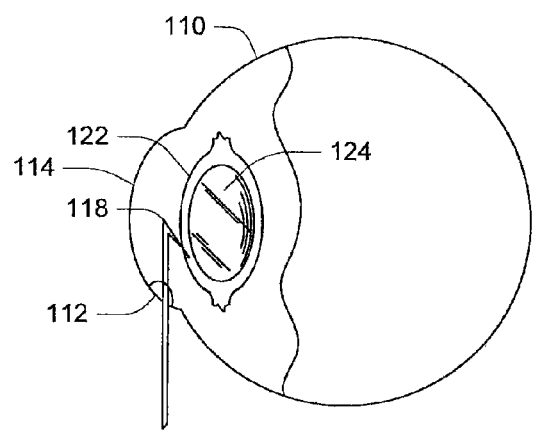
FIG. 3 is a cross-sectional view of a human eyeball further illustrating the prior art method of performing an anterior capsulotomy.
Figure 4:
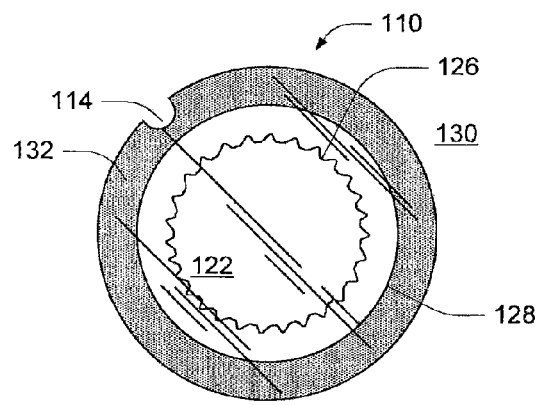
FIG. 4 is a front view of a cornea after an anterior capsulotomy is performed according to the prior art method.

As further depicted in FIG. 2, a stylet or needle 116 having a bend 118 such that the head 120 of stylet or needle 116 can be inserted through incision 112. As can be seen in FIG. 3, head 120 of stylet or needle 116 is then used to make small, overlapping tears in anterior capsule 122 to form an opening that can be used to remove the original lens 124 and insert an artificial one. Specifically, the process requires the repeated puncturing of anterior capsule 122 with head 120 of stylet or needle 116 and pulling on the stylet or needle 116, each time making small tear in the anterior capsule 122. As shown in FIG. 4, this repeated tearing of anterior capsule 122 forms a jagged opening 126 in anterior capsule 122.

Figure 5A:
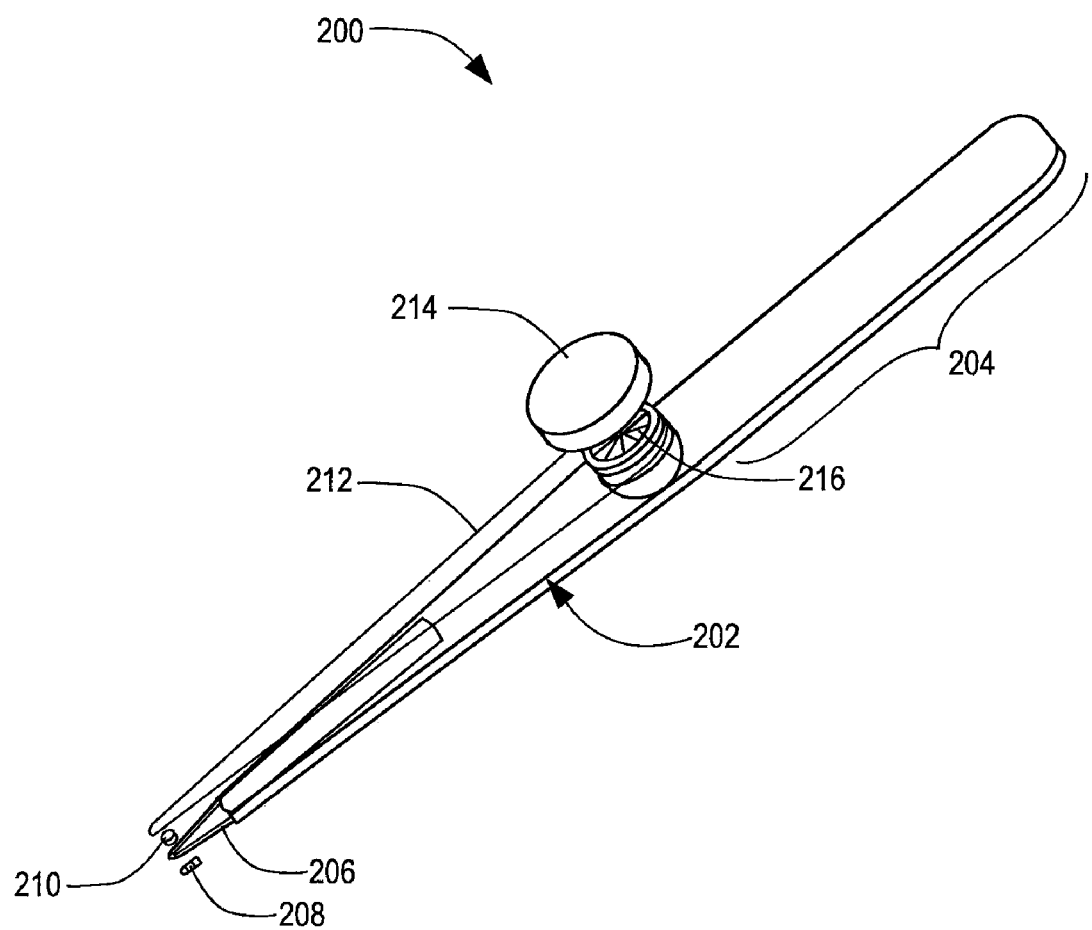
FIG. 5A is a perspective view of an exemplary anterior capsulotomy device of the present invention.
Figure 5B:
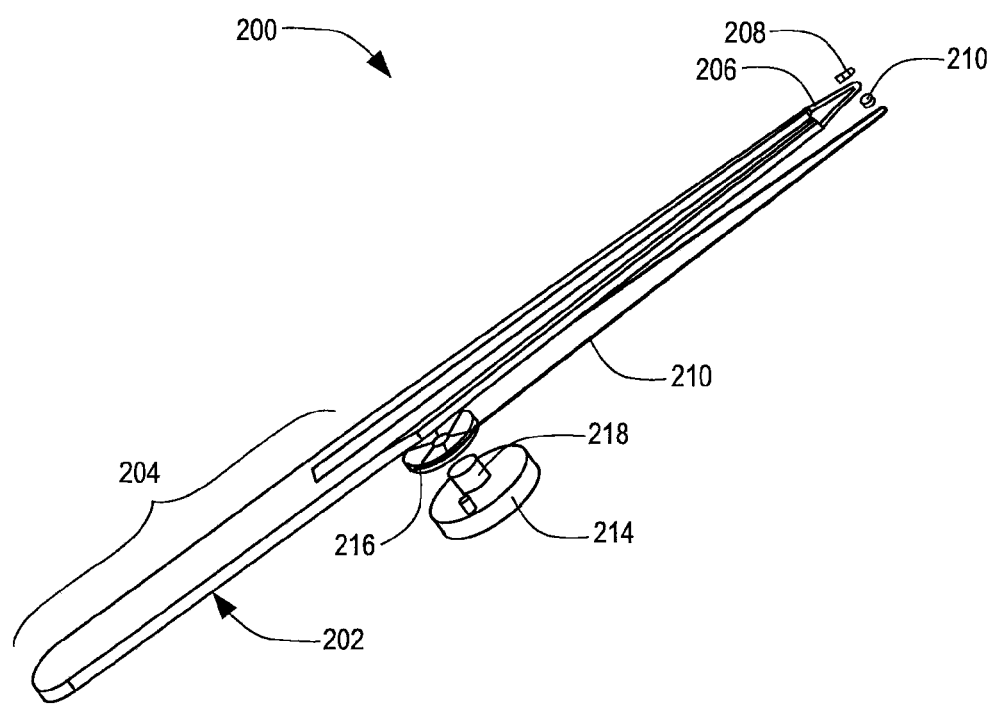
FIG. 5B is a perspective view of the underside of the exemplary anterior capsulotomy device of FIG. 5A.

With the foregoing background information, the operation and utility of the instrument of the present invention may now be explained and fully understood. Referring now to FIGS. 5A and 5B, the anterior capsulotomy device 200 of the present invention generally comprises a body 202, wherein the proximal end is tapered to a head 206 and the distal end acts as a handle portion 204. Device 200 further comprises a front pulley 210 connected to a cutting element 208, wherein a portion of front pulley 210 extends through an opening in head 206 to attach to cutting element 208.

Actuator 214 is attached to body 202 such that actuator 214 can be moved by a thumb of a user. Actuator 214 is connected to rear pulley 216 via connecting element 218 (FIG. 5B only) such that, when moved, actuator 214 causes rear pulley 216 to rotate. Rear pulley 216 is in turn connected to front pulley 210 by connecting element 212, such that rotation of rear pulley 216 causes rotation of front pulley 210 and cutting element 208.

In certain embodiments, connecting element comprises a continuous assembly. In certain embodiments, connecting element 212 comprises a cable. In other embodiments, connecting element 212 comprises a belt. In yet other embodiments, connecting element 212 comprises a cord. In certain embodiments, connecting element 212 is formed from a plastic. In other embodiments, connecting element 212 comprises a metal.

As depicted in FIGS. 5A and 5B, actuator 214 is mechanically operated by a thumb of a user. In certain embodiments, actuator 214 is rotated by the user. In other embodiments, actuator 214 is depressed by the user. As will be clear to one of ordinary skill in the art, other types of actuators may be used in place of actuator 214 without departing from the scope of the disclosure.

In the illustrated embodiment of FIG. 5B, body 202 is illustrated as being formed to include groove 220. In other embodiments, anterior capsulotomy device 200 is not formed to include such a groove.

Figure 6:
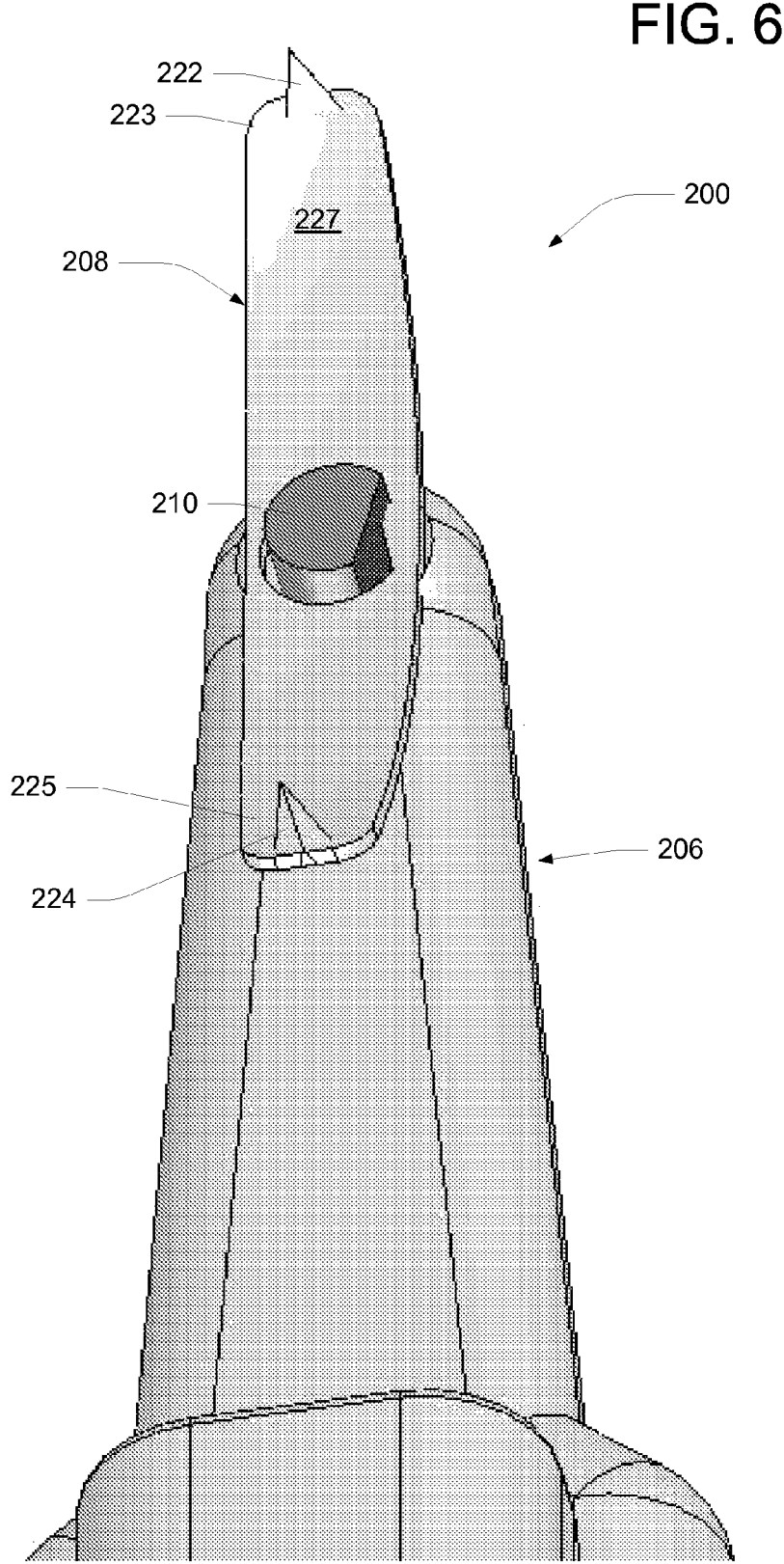
FIG. 6 is a detailed view of the head of the exemplary anterior capsulotomy device of FIG. 5A.
Figure 7:
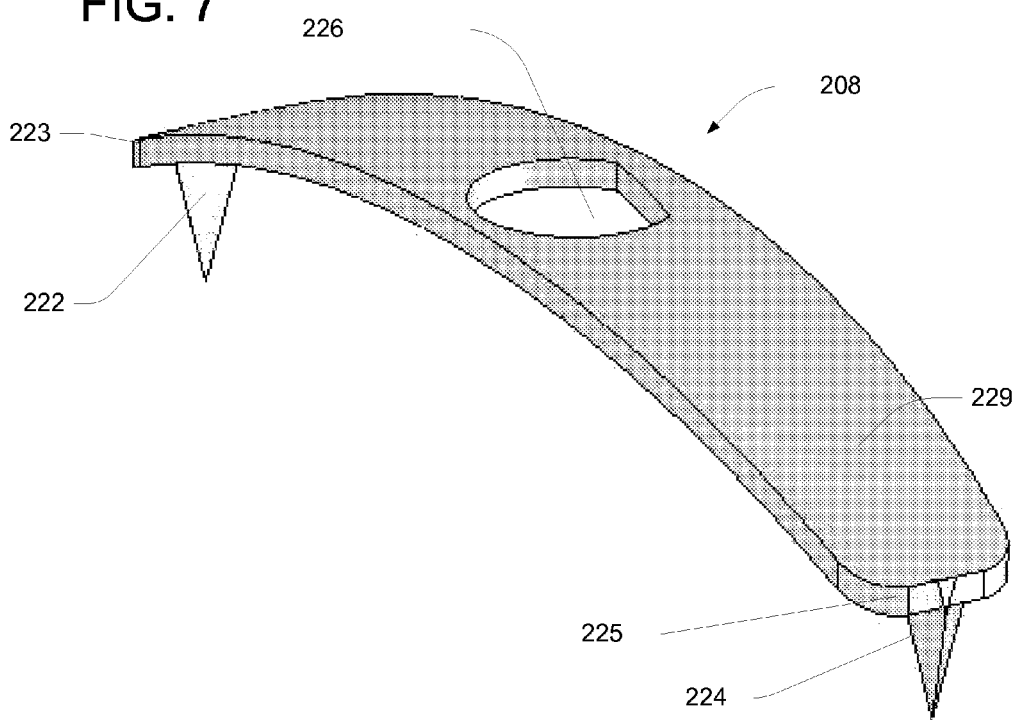
FIG. 7 is a detailed view of the cutting element of the exemplary anterior capsulotomy device of FIG. 5A.

Referring now to FIGS. 6 and 7, cutting element 208 is rotatably disposed on head 206 and is attached thereto by front pulley 210. Member 408 (FIG. 8) is attached to front pulley 210, and extends through head 206, and couples to the periphery of aperture 226 (FIG. 7) formed in cutting element 208, thereby securing cutting element 208 to head 206 while allowing cutting element 208 to rotate with front pulley 210.

In the illustrated embodiments of FIGS. 6 and 7, cutting element 208 comprises a first surface 227, a second surface 229, and two (2) surgical blades, namely blade 222 and blade 224, disposed on opposite ends, first end 223 and second end 225, of cutting element 208 and projecting in a downward direction. In certain embodiments, blades 222 and 224 are formed on cutting element 208 such that cutting element 208 and blades 222 and 224 are a single, contiguous formation. In other embodiments, blades 222 and 224 are disposed on cutting element 208.

In certain embodiments, only the leading edges of blades 222 and 224 are cutting edges. In other embodiments, both the leading and trailing edges of blades 222 and 224 are cutting edges. In such an embodiment, cutting element 208 may be rotated in either a clockwise or counterclockwise direction without affecting the device's ability to cut the anterior capsulotomy.

In certain embodiments, blades 222 and 224 comprise one or more metals. In certain embodiments, blades 222 and 224 comprise the same substance as cutting element 208. In yet other embodiments, blades 222 and 224 comprise a different substance than cutting element 208.

Figure 8:
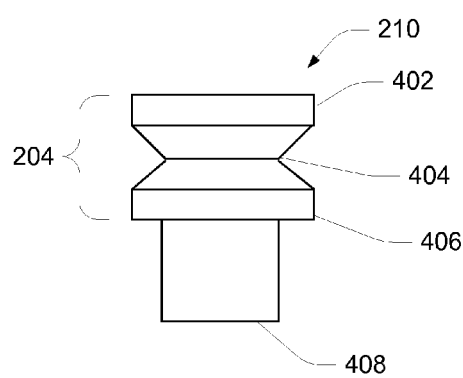
FIG. 8 is a detailed view of the front pulley of the exemplary anterior capsulotomy device of FIG. 5A.
Figure 9A:
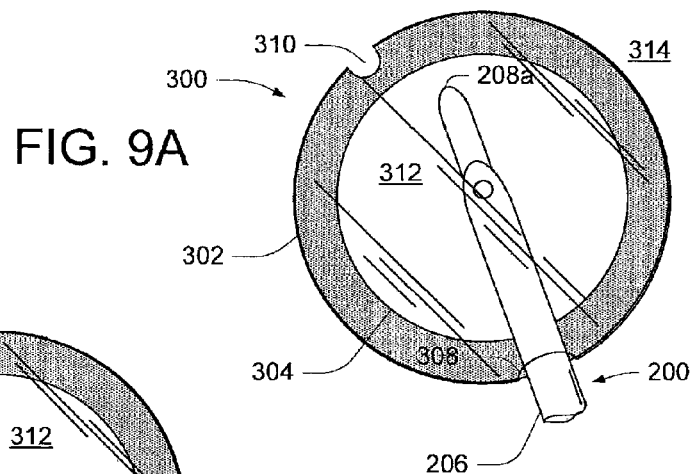
FIG. 9A depicts the insertion of the exemplary anterior capsulotomy device of FIG. 5A in a limbal incision.
Figure 9B:
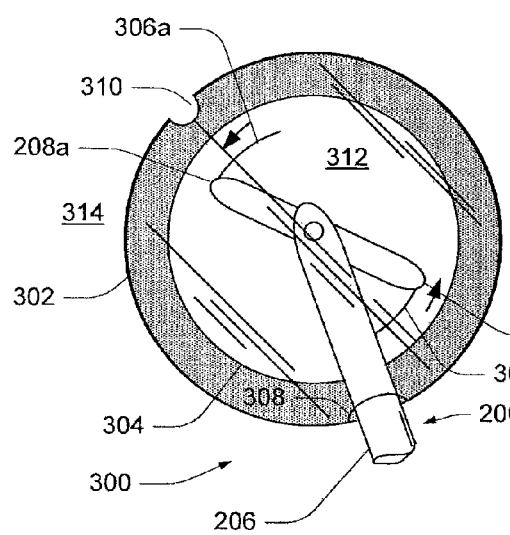
FIG. 9B depicts the process of making an incision in the anterior capsulotomy using the exemplary anterior capsulotomy device of FIG. 5A.
Figure 9C:
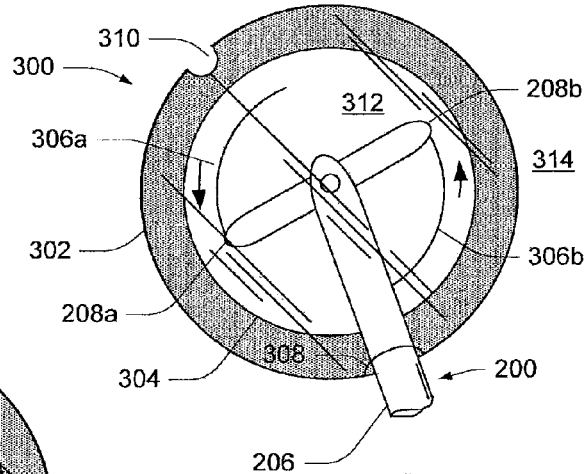
FIG. 9C provides another view of the process of making an incision in the anterior capsulotomy using the exemplary anterior capsulotomy device of FIG. 5A.
Figure 9D:
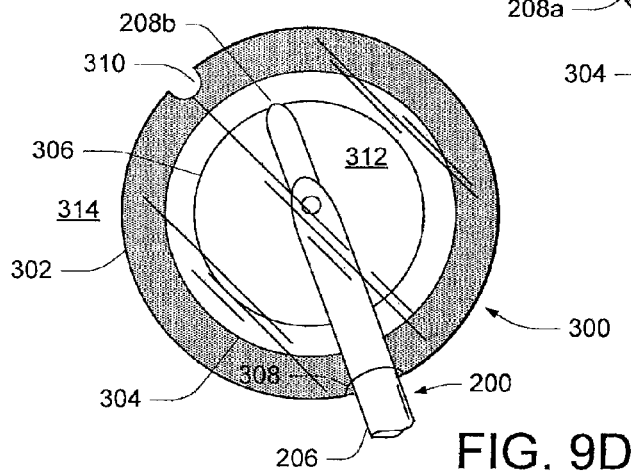
FIG. 9D depicts the completion of a circular incision in the anterior capsulotomy made using the exemplary anterior capsulotomy device of FIG. 5A.

Turning to FIG. 8, the exemplary embodiment of front pulley 210 is shown as having member 408, which extends through head 206 (FIGS. 5A, 5B, and 6) and aperture 226 (FIG. 7) to secure cutting element 208 (FIGS. 5A, 5B, 6, and 7) to head 206. As will be understood by one of ordinary skill in the art, cutting element 208 may be rotatably attached to head 206 by a means other than front pulley 210 without departing from the scope of the disclosed invention.

In certain embodiments, front pulley 210 is formed such that member 408 is substantially cylindrical having one flat side (illustrated in FIG. 6) that abuts a flat side of aperture 226 (FIG. 7). In other embodiments, member 408 and aperture 226 may have other configurations.

As illustrated in FIG. 8, front pulley 210 additionally comprises sheave 410 formed to include groove 404 disposed between upper flange 402 and lower flange 406 along the circumference of sheave 410. When connecting cutting element 208 (FIGS. 5A, 5B, 6, and 7) to head 206 (FIGS. 5A, 5B, and 6), lower flange 406 rests on top of head 206 while member 408 extends through head 206 and into aperture 226 (FIG. 7). Connecting element 212 (FIGS. 5A and 5B) then rests within groove 404.

One feature of the present invention is that the cutting element does not need to make a full 360 degree rotation when actuated by the actuator. Rather, the cutting element can make a circular incision by being rotated about 180 degrees. In certain embodiments, the cutting element comprises two blades, such as blades 222 and 224 (FIGS. 6 and 7), located at opposing ends of the cutting element. In these embodiments, the rotation causes each blade to make a contiguous semicircle incision of a predetermined diameter. In certain embodiments, the cutting element is rotated more than 180 degrees, and therefore, the ends of each semicircle overlap to form a single, circular incision.

The amount of the overlap is small to prevent and/or minimize tearing of the anterior capsulotomy in the area of the overlap. As is known by one of ordinary skill in the art, repeatedly cutting the same area of the anterior capsule wall increases the likelihood of tearing. In one embodiment, the arcs cut by each blade of the cutting element overlap by two (2) degrees at either end. In such an embodiment, the cutting element rotates 182 degrees when actuated.

As will be clear to one of ordinary skill in the art, by having two opposing surgical blades, the overall sheer stress experienced by the anterior capsule wall is minimal compared to the sheer stress created by a cutting instrument having a single blade. As is known by one of ordinary skill in the art, sheer stress causes deformation of a material by slippage along a plane parallel and/or tangential to the imposed stress. This deformation increases the likelihood that the anterior capsule wall will tear. By utilizing two surgical blades, each moving in opposite directions at the same time and applying the same stress, each blade generates a sheer stress of equal value in opposing directions, thereby theoretically resulting in a net sheer stress of zero. As will be understood by one of ordinary skill in the art, the natural presence of imperfections, varying thickness, etc. will result in an actual net sheer stress that is slightly greater than zero.

As will be apparent to one of ordinary skill in the art, the diameter of the cut made by the cutting element is equal to the distance between the two blades. In certain embodiments, this distance is adjustable. In other embodiments, the disclosed anterior capsulotomy device may come in varying sizes, each having a different distance between the blades. Alternatively, the cutting head may be interchangeable; different cutting heads having blades spaced different lengths apart.

Turning now to FIGS. 9A-9D and 10, the manner of performing a capsulotomy using the present invention is illustrated. Each of the figures depict a human eye 300 having an anterior capsule 312 exposed through the pupil 304 of the overlying iris 302, and the sclera 314 circumferentially surrounding iris 302. The cornea 310 overlies anterior capsule 312, pupil 304, and iris 302. Initially, head 206 of the disclosed device is inserted through a small limbal incision 308 and the cutting element is placed in contact with the anterior capsule wall 304. In certain embodiments, head 206 is alternatively inserted through a clear corneal incision. By using the actuator (not shown), the cutting element is rotated in the manner depicted in FIGS. 9B-9D. The blades at ends 208a and 208b of the cutting element cut opposing arcs 306a and 306b, shown in FIGS. 9B and 9C. As discussed, the cutting element makes a slightly greater then 180 degree rotation thereby causing arcs 306a and 306b to overlap, forming circular opening 306 shown in FIG. 9D. At this point, head 206 is withdrawn and the cut portion of the anterior capsulotomy wall may then be removed through limbal incision 308 using a probe or other device.

While the preferred embodiments of the present invention have been illustrated in detail, it should be apparent that modifications and adaptations to those embodiments may occur to one skilled in the art without departing from the scope of the present invention.

What is claimed is:

1. A device for performing an anterior capsulotomy procedure, the device comprising:
   a body having a proximal end and a distal end;
   a rotatable cutting element rotatably disposed on the proximal end of the body, wherein the cutting element comprises a plurality of surgical blades and an arcuate member, wherein the arcuate member has a first end, a second end, a first surface, and a second surface, wherein the first end of the arcuate member opposes the second end of the arcuate member, wherein the first surface opposes the second surface, wherein a first surgical blade is attached to the first end of the arcuate member and extends outwardly there from, wherein a second surgical blade is attached to the second end of the arcuate member and extends outwardly there from
   a shaft having a first end and a second end;
   a first pulley, wherein the proximal end of the body is formed to include an aperture extending there through, wherein the shaft is rotatably disposed through the aperture, wherein the first pulley is attached to the first end of the shaft, wherein the second end of the shaft is attached to the second surface of the arcuate member; and
   an actuator, wherein the actuator is movable between a first position and a second position, wherein the actuator is operatively coupled to the rotatable cutting element such that when the actuator is moved from the first position to the second position the arcuate member is rotated about 180 degrees.

2. The device of claim 1, further comprising a second pulley operatively coupled to the actuator, wherein a first end of a fixed length of material is anchored to the first pulley and a second end of the fixed length of material is anchored to the second pulley.

3. The device of claim 2, further comprising a handle disposed between the distal end of the body and the actuator.

4. The device of claim 1, further comprising a second pulley operatively coupled to the actuator, wherein an endless belt interconnects the first pulley and the second pulley.

5. The device of claim 1, wherein the actuator is manually operated.

6. The device of claim 5, wherein the actuator is a finger trigger.

7. The device of claim 5, wherein the actuator is a rotatable knob.

8. The device of claim 1, wherein the arcuate member can be rotated about 182 degrees.

9. The device of claim 1, wherein the device is disposable after a single use.

* * * * *